United States Patent
Robertson et al.

(10) Patent No.: US 7,912,527 B2
(45) Date of Patent: Mar. 22, 2011

(54) PASSIVE SUBCUTANEOUS BODY-TEMPERATURE MEDICAL IMAGING APPARATUS

(75) Inventors: Duncan Alexander Robertson, Keltybridge (GB); David Graham MacFarlane, Alyth (GB); James Christopher George Lesurf, St. Andrews (GB)

(73) Assignee: The University Court of the University of St. Andrews, St. Andrews (GB)

( * ) Notice: Subject to any disclaimer, the term of this patent is extended or adjusted under 35 U.S.C. 154(b) by 1303 days.

(21) Appl. No.: 10/509,509

(22) PCT Filed: Mar. 26, 2003

(86) PCT No.: PCT/GB03/01284
§ 371 (c)(1),
(2), (4) Date: Apr. 28, 2005

(87) PCT Pub. No.: WO03/082090
PCT Pub. Date: Oct. 9, 2003

(65) Prior Publication Data
US 2005/0228265 A1    Oct. 13, 2005

(30) Foreign Application Priority Data
Mar. 28, 2002 (GB) .................. 0207370.8

(51) Int. Cl.
*A61B 5/00* (2006.01)
(52) U.S. Cl. ............ 600/407; 250/339.04; 374/100
(58) Field of Classification Search ............ 600/474, 600/475, 412, 407, 425; 374/9, 32, 100, 374/120–133; 250/339.04; 342/692, 702; 343/786
See application file for complete search history.

(56) References Cited

U.S. PATENT DOCUMENTS

| | | | | |
|---|---|---|---|---|
| 3,622,888 A * | 11/1971 | Robert et al. | ............... | 324/76.14 |
| 4,346,716 A * | 8/1982 | Carr | ............................ | 600/407 |
| 4,366,381 A * | 12/1982 | Fischer et al. | ............. | 250/316.1 |
| 4,407,292 A * | 10/1983 | Edrich | ......................... | 600/430 |
| 4,545,653 A * | 10/1985 | Brenden et al. | ............... | 359/719 |
| 4,557,272 A * | 12/1985 | Carr | ............................ | 600/549 |
| 4,641,659 A * | 2/1987 | Sepponen | ..................... | 600/430 |
| 4,774,961 A * | 10/1988 | Carr | ............................ | 600/549 |
| 4,798,209 A * | 1/1989 | Klingenbeck et al. | ......... | 600/430 |
| 4,805,627 A * | 2/1989 | Klingenbeck et al. | ......... | 600/425 |
| 4,852,973 A * | 8/1989 | Durnin et al. | .................. | 359/559 |
| 4,864,308 A * | 9/1989 | Raab et al. | .................... | 342/351 |
| 5,020,920 A * | 6/1991 | Gopalsami et al. | ............. | 374/57 |
| 5,047,783 A * | 9/1991 | Hugenin | ....................... | 342/179 |
| 5,176,146 A * | 1/1993 | Chive et al. | ................... | 600/549 |
| 5,231,404 A * | 7/1993 | Gasiewski | .................... | 342/351 |

(Continued)

OTHER PUBLICATIONS

Robert K. Cacak, Daniel W. Winans, Jochen Edrich and William R. Hendee, "Millimeter Wavelength Thermographic Scanner", Med. Phys. 8(4), Jul./Aug. 1981.*

(Continued)

*Primary Examiner* — Brian Casler
*Assistant Examiner* — Parikha S Mehta

(57) ABSTRACT

A medical imaging apparatus for imaging subcutaneous body temperature that comprises a detector (22) for sensing millimeter wave electromagnetic radiation and a collector for collecting radiation emitted from a patient's body and directing it along a collection path (20) to the detector. The collector is configured so that the collected radiation has a defined sensitivity profile across and along substantially the entire length of that path. The collected radiation may have a Gaussian or a Bessel sensitivity profile.

23 Claims, 14 Drawing Sheets

U.S. PATENT DOCUMENTS

| | | | | |
|---|---|---|---|---|
| 5,688,050 | A | * | 11/1997 | Sterzer et al. .................. 374/122 |
| 5,760,397 | A | * | 6/1998 | Huguenin et al. ............. 250/332 |
| 5,785,426 | A | * | 7/1998 | Woskov et al. ............... 374/126 |
| 5,807,257 | A | * | 9/1998 | Bridges .......................... 600/430 |
| 5,829,437 | A | * | 11/1998 | Bridges .......................... 600/430 |
| 5,900,837 | A | * | 5/1999 | Petrosian ....................... 342/368 |
| 5,953,644 | A | * | 9/1999 | Kool et al. ..................... 455/328 |
| 5,983,124 | A | * | 11/1999 | Carr ................................ 600/407 |
| 6,052,024 | A | * | 4/2000 | Lo et al. .......................... 330/53 |
| 6,469,820 | B1 | * | 10/2002 | Mushiake et al. ............. 359/215 |
| 6,777,684 | B1 | * | 8/2004 | Volkov et al. .............. 250/341.1 |
| 2007/0257188 | A1 | * | 11/2007 | Robertson et al. ......... 250/252.1 |

OTHER PUBLICATIONS

Roger Appleby, David G. Gleed and Rupert N. Anderton, "High Performance Passive Millimeter Wave Imaging", Defense Research Agency, St. Andrews Rd., Gt. Malvern, Worcs WR14 3PS, UK. Alan H. Lettington, J.J. Thomson, Physical Laboratory, Reading University, Whitenights, PO Box 220, Reading, RG6 2AF, UK.*

J. Edrich et al., "Imaging Thermograms at Centimeter and Millimeter Wavelengths", Annals New York Academy of Sciences. 1980, pp. 456-474.*

Wylde RJ. Millimetre-wave Gaussian beam-mode optics and corrugated feed horns (Abstract only). IEEE Proceedings, part H—Microwaves, Optics and Antennas. vol. 131, part H, No. 4 p. 258-262. Aug. 1984.*

International Search report for PCT/GB03/01284 completed Jul. 11, 2003.

Roger Appleby, David G. Gleed and Rupert N. Anderton, "High Performance Passive Millimetre Wave Imaging", Defence Research Agency, St. Andrews Rd., Gt. Malvern, Worcs WR14 3PS, UK. Alan H. Lettington, J.J. Thomson, Physical Laboratory, Reading University, Whiteknights, PO Box 220, Reading, RG6 2AF, UK, Jun. 1993.

S. Gabriel, R. W. Lau and C. Gabriel, "The Dielectric Properties of Biological Tissues: III. Parametric Models for the Dielectric Spectrum of Tissues", Physics Department, King's College, Strand, London WC2R 2LS, UK Phys. Med. Biol. 41 (1996) 2271-2293.

C. Gabriel, S. Gabriel and E. Corthout, "The Dielectric Properties of Biological Tissues: I. Literature Survey", Phys. Med. Biol. 41 (1996) 2231-2249.

S. Gabriel, R. W. Lau and C. Gabriel, "The Dielectric Properties of Biological Tissues: II. Measurements in the Frequency Range 10 Hz to 10 GHz", Phys. Med. Biol. 41 (1996) 2251-2269.

Robert K. Cacak, Daniel W. Winans, Jochen Edrich and William R. Hendee, "Millimeter Wavelength Thermographic Scanner", Med. Phys. 8(4), Jul./Aug. 1981.

B. Bocquet, J.C. Van De Vlede, A. Mamouni, Y. Leroy, G. Giaux, J. Delannoy and D. Delvalee, "Microwave Radiometric Imaging at 3 GHz for the Exploration of Breast Tumors", IEEE Transactions on Microwave Theory and Techniques, vol. 38, No. 6, Jun. 1990.

David M. Sheen, Douglas L. McMakin and Thomas E. Hall, "Three-Dimensional Millimeter-Wave Imaging for Concealed Weapon Detection", IEEE Transactions on Microwave Theory and Techniques, vol. 49, No. 9, Sep. 2001.

* cited by examiner

Fundamental Mode Gaussian Beam Propagation

Visible

Infrared mm-wave

PASSIVE SUBCUTANEOUS BODY-TEMPERATURE MEDICAL IMAGING APPARATUS

This invention relates to a medical imaging apparatus for imaging subcutaneous temperature within a body.

Medical imaging using infrared imaging or thermography to obtain passive and non-invasive measurements of human body temperature is an established technique. This technique is, however, relatively limited, because infrared imaging only effectively measures the surface temperature of the body. This is because infrared radiation does not penetrate body tissue very well, and it is difficult to ascertain sub-surface temperature distributions accurately from such surface temperature measurements.

Microwave thermography is often used where tissue temperature at depth within bodies is to be measured, see for example the article "Microwave Radiometric Imaging at 3 GHz for the Exploration of Breast Tumors" by Bocquet et al, IEEE Transactions on Microwave Theory and Techniques, Vol 38, No. 6, June 1990. Typically, microwave thermography is done using a contact-probe radiometer operating at a frequency of around 2-3 GHz. Since microwaves can travel further through body tissues, microwave thermography can achieve measurements to a depth of several centimeters. However, whilst temperature contributions are detectable at depth, spatial resolution is generally poor. This is because of the relatively long wavelengths.

U.S. Pat. No. 4,407,292 discloses another imaging technique. In this, thermal radiation emitted by hyperthermic tumerous tissues is collected, focussed and detected within several frequency bands from 8 GHz to 36 GHz. This is done using a lightweight elliptical reflector and a broadband radiometer. A problem with the arrangement of U.S. Pat. No. 4,407,292 is, however, that the spatial resolution is poorly defined. Additionally, the image acquisition time is long, due to the relative insensitivity of the receiver.

An object of the present invention is to overcome one or more of the disadvantages associated with the prior art.

According to one aspect of the invention, there is provided a passive medical imaging apparatus for imaging subcutaneous body temperature, the apparatus comprising a detector for sensing millimeter wave electromagnetic radiation and a collector for collecting radiation emitted from a patient's body and directing it along a collection path to the detector in such a manner that the collected radiation has a defined sensitivity profile across and along substantially the entire length of that path.

By providing a sensitivity profile that is defined along the entire length of the collection path, improved knowledge of the beam that is incident on the detector is provided. This is because radiation received from the area on which the device is focused has propagated in a well-controlled and definable pattern. This information can then be used through signal processing to improve the overall spatial resolution of the image.

In this context, the sensitivity profile is defined in that its general form is known along the whole of the collection path. One example of such a general form of profile is a fundamental Gaussian profile.

Preferably, the collector comprises focussing means. The collector and/or focussing means can be considered to act as an antenna. The collector may comprise a feedhorn, in particular a corrugated feedhorn, and a wave guide for supplying radiation to the detector, the feedhorn being arranged to convert a fundamental Gaussian mode beam of radiation, created by the collector and/or focussing means, into a wave guide mode in which radiation propagates through the wave guide to the detector. In this way, the feedhorn achieves a fundamental Gaussian mode sensitivity profile. Alternatively, the apparatus may have a Bessel sensitivity profile and to that end may include an axicon. This axicon is a cylinder formed with a conical prism at one end.

Preferably, the collector is operable repeatedly to sweep the collection path through 360°. To this end, the collector may comprise a deflector that is rotatable about one axis to scan the collection path in a scanning direction. Alternatively, the collector may be linearly movable, so as to provide a raster scan. In either case, the apparatus can further comprise line-indexing means for moving the collection path in a direction perpendicular to the scanning direction. The indexing means may move the deflector linearly along said axis or may comprise means for swinging the deflector about a second axis perpendicular to the first axis. An advantage of this is that it avoids the need to move the whole of the imaging apparatus relative to the body in order to scan the portion of the body to be imaged.

Preferably, the apparatus further comprises an isolator situated, in use, in the radiation collection path for preventing signal leakage from the apparatus into the collection path. This feature is useful if the apparatus is used on close range subjects. The isolator prevents leakage of radiation from the apparatus, which when reflected back off the target could degrade the sensitivity.

Where the apparatus includes a feedhorn, the isolator may be interposed between the feedhorn and the detector or in front of the horn. By doing the latter, that is placing the isolator between detector and the feedhorn, it is easier to achieve low insertion loss over a wide bandwidth, which is necessary for good thermal sensitivity.

Preferably, the apparatus is operable to form an image from emitted radiation in the frequency range of 10-200 GHz, for example 90-100 GHz.

The apparatus may be sensitive to radiation of a plurality of different frequencies. This enables the apparatus to resolve areas of thermal emission in three dimensions.

Preferably, the apparatus includes calibration load means for emitting millimeter wave radiation at a pre-determined intensity, the apparatus being operable to direct said radiation to the detector to enable the apparatus to be calibrated. The calibration load may be provided in the scanning path of the imager, so that it is scanned each time the target is scanned. In this way, the imager can be calibrated for each pass of the imager. Where the collection path is rotatable, the load means may be positioned so as to lie in a line swept by the rotating collection path so that the apparatus can be calibrated for each individual sweep. Where the collection path is a raster scan path, the load means may be provided at one or more ends of the raster scan path, so that the load is scanned each time a line is scanned. The load means may comprise two loads and means for maintaining them at different temperatures. Preferably, the calibration load temperatures straddle the range of subcutaneous body temperatures to be imaged.

If the detector is linearly polarised, the apparatus preferably includes polarisation means for altering the polarisation of received radiation so as to align with the polarisation of the detector.

According to another aspect of the invention, there is provided an apparatus having a detector that is sensitive to millimeter wavelengths of electromagnetic radiation; a collector for collecting such radiation emitted from an area of a body and directing it towards the detector, the collector being movable along a collection path and calibration means located in the collection path operable to emit radiation of a known intensity.

By providing a calibration load in the collection path of the collector, calibration data can be obtained every time the collector moves along the collection path. This means that the imager can be calibrated on a line-by-line basis. This is advantageous.

According to a further aspect of the invention there is provided a medical imaging apparatus for imaging subcutaneous body temperatures, the apparatus comprising a detector sensitive to millimeter wave electromagnetic radiation and for generating an output representative of the image; a collector for collecting radiation from a selected body to be imaged and directing the radiation to the detector, and an isolator situated in the radiation path to the detector and operable to prevent interfering electromagnetic radiation generated by the detector from being emitted from the device via the collector means, whilst allowing received radiation to reach the detector. The isolation means may comprise a quasioptical isolator.

In accordance with still another aspect of the invention, there is provided a medical imaging apparatus for imaging subcutaneous body temperatures, the apparatus comprising a detector sensitive to incident millimeter wave electromagnetic radiation and for generating an output representative of the image; a collector for collecting such radiation travelling from a selected area of a body to be thermally imaged to the collector along a collection path and directing said radiation onto the detector means, and a scanner for causing said path to rotate.

By providing a scanner to allow the collection path to be rotated, the selected area of the body or region thereof can be thermally imaged relatively rapidly.

Preferably, the apparatus includes focussing means for focussing the detector means on said area, wherein the focussing means is such as to give the apparatus a defined sensitivity profile across and along substantially the entire path length.

Various aspects of the invention will now be described, by way of example only, with reference to the accompanying drawings in which.

Figure 1:
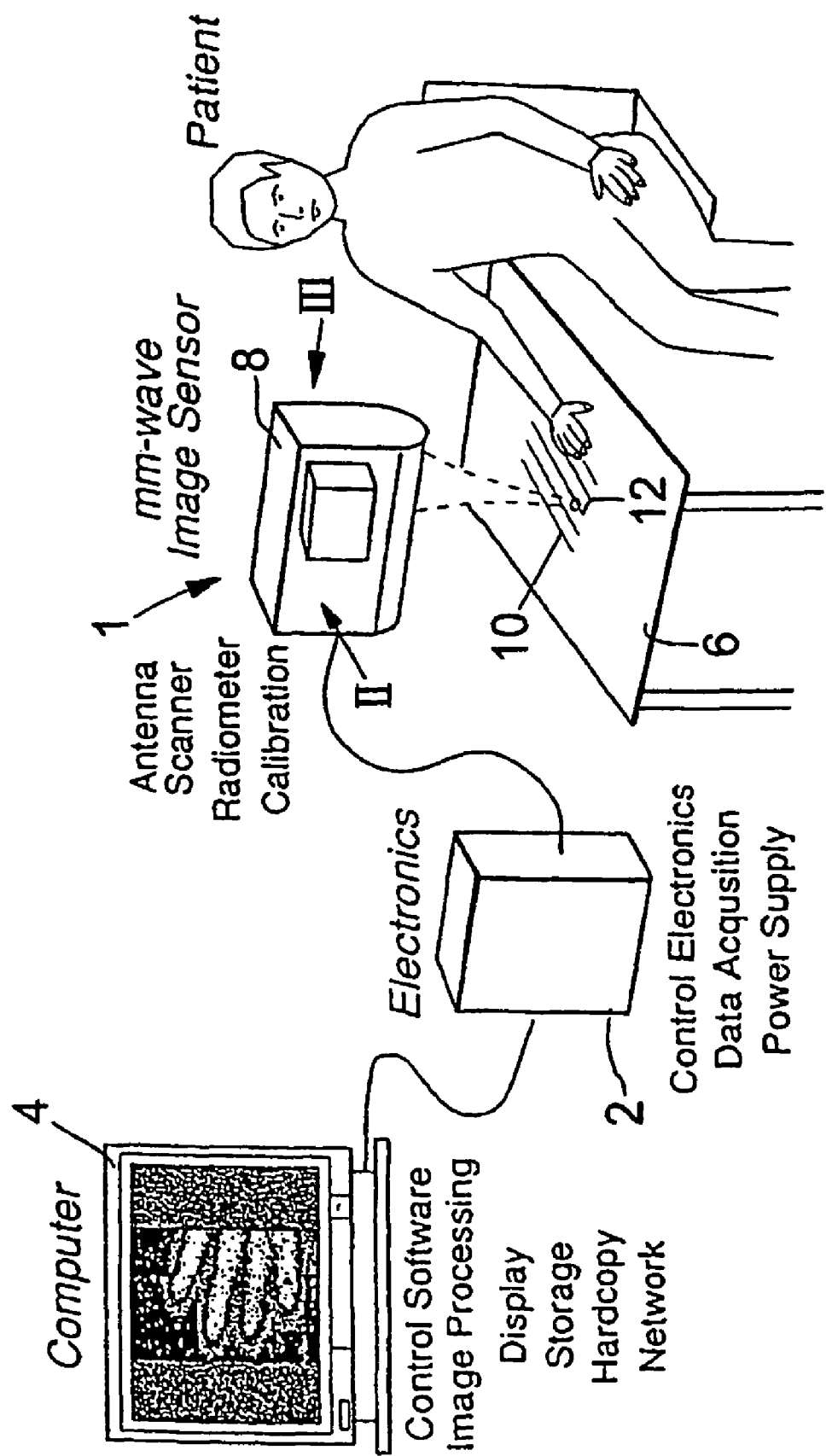
FIG. 1 is a schematic diagram of a first medical imaging apparatus including a passive millimeter radiometer.

FIG. 1 shows a passive imager 1 that is operable to detect millimeter wavelength radiation emitted from the body. By passive it is meant that no radiation is directed onto the patient by the imager. Instead the imager is operable to detect radiation that is naturally emitted from the patient's body. The imager is connected to electronic circuitry 2 for controlling and supplying electrical power thereto and also receiving image data therefrom. Received data is processed and displayed as an image on a computer 4. The imager 1 is positioned a few tens of centimeters directly above a tabletop 6 on which a part of the patient to be imaged is rested, in this case the hand. The components of the imager 1 are contained within a housing 8 that has a lower window (not shown) through which an area of the tabletop 6 can be scanned, in order to obtain the image. The apparatus scans the area in a succession of parallel lines, such as lines 10 and 12.

Figure 2:
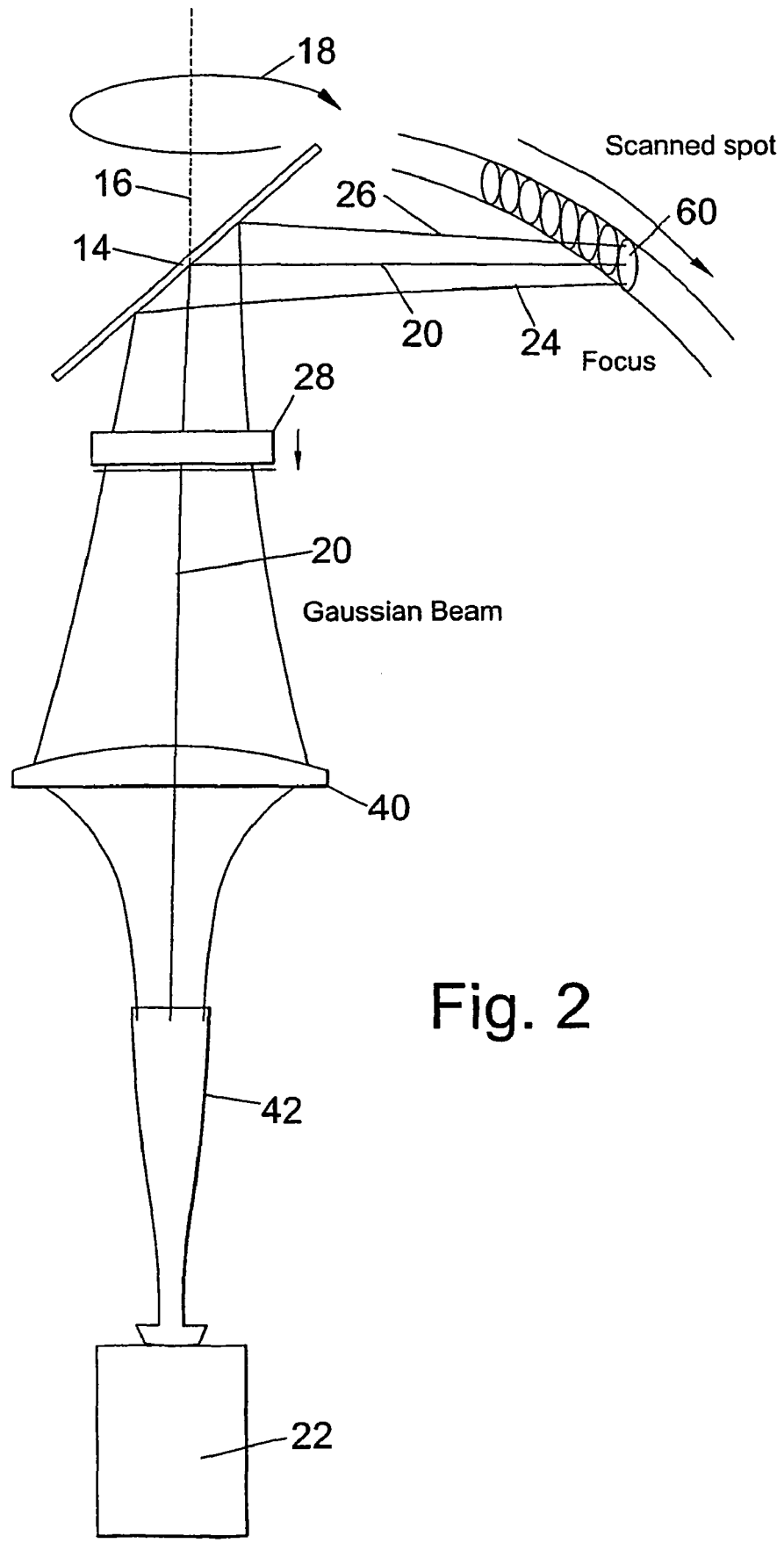
FIG. 2 is a block diagram of a scanner for use in the radiometer of FIG. 1.

FIG. 2 shows the imager 1 of FIG. 1 in more detail. This comprises a planar mirror 14 that is rotatably mounted about an axis 16. Optionally, the mirror 14 may be rotatable about two separate axes (not shown). Connected to the mirror 14 is a motor (not shown), which is operable to rotate the mirror in the direction indicated by the arrow 18. The mirror 14 is in registry with the window in the housing 8 and is provided to scan an area of the patient and direct millimeter radiation received from that area into a main optical path 20 and towards a detector 22. As an example, the radiometer may be a 95 GHz heterodyne total power radiometer 22.

On the optical path between the mirror 14 and the detector 22 is a quasi-optical isolator 28. This is provided to prevent signals leaking out from the apparatus. Certain types of radiometer, especially heterodyne designs, can leak local oscillator (LO) signals out of the input port of the mixer of the radiometer. This can be coupled out via the antenna towards the subject/target, which can degrade the performance of the radiometer by causing fluctuations in its sensitivity. This can be misinterpreted as radiation emitted by the target. Providing an isolator 28 avoids this effect.

Figure 3:
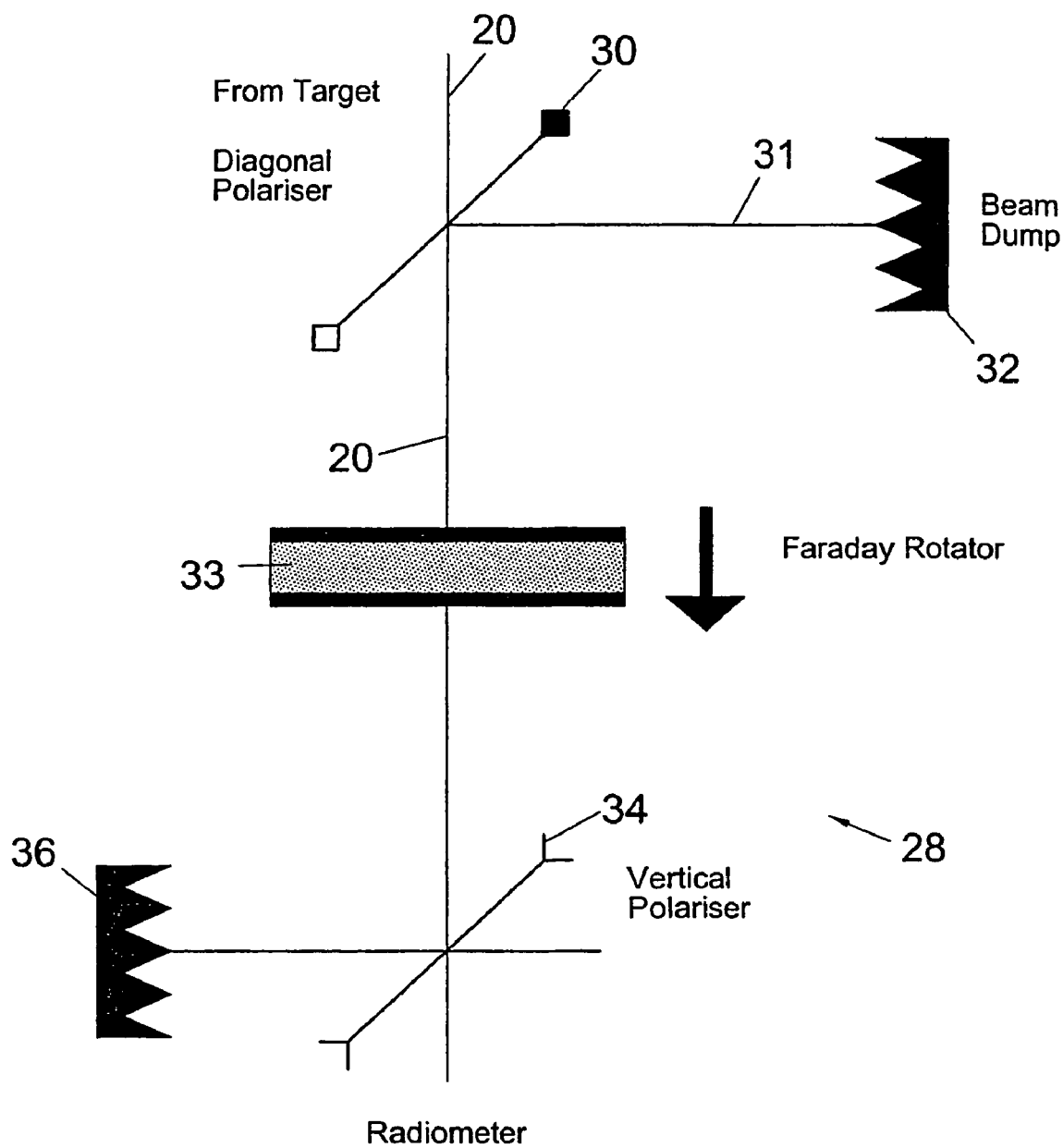
FIG. 3 is a block diagram of a quasi-optical isolator for use in the imager of FIG. 2.

The isolator 28 can take any suitable form, but a preferred version is shown in FIG. 3. This comprises a diagonal polariser 30, which lies on the optical path 20. Facing the polariser 30 and on a line 31 that is substantially perpendicular to the main optical path is a surface 32 that is able to absorb radiation of the frequency of interest. This will be referred to as a "beam dump" 32. Downstream of the diagonal polariser and on the main path 20 is a Faraday rotator 33, after which is another polariser 34, in this case a vertical polariser. Facing this second polariser 34 is a corresponding off-axis beam dump 36. The diagonal polariser 30 is orientated to allow the passage of light with a polarisation at 45° to that of light passed by the vertical polariser 34.

The isolator of FIG. 3 acts as a four-port circulator in which two ports are terminated. Electromagnetic radiation of the desired frequency selected by the apparatus is passed through the isolator. However, any local oscillator leakage from the radiometer is sent to the beam dump 32. Any signals coming from the dump 32 go to the dump 36 and any stray signal from the dump 36 would go to the main path 20.

Radiation emitted from the isolator 28 is directed into focussing means, for example a high-density polyethylene lens 40 and from there, into a feedhorn, in particular a corrugated feedhorn 42, as shown in FIG. 2. The lens 40 is adapted to focus on a spot on a cylindrical object plane for a given position of the mirror 14 and direct radiation emitted from that spot to the feedhorn 42. Radiation focussed by the lens 40 on the feedhorn 42 takes the form of a substantially fundamental Gaussian mode beam. This has a well-defined profile across and along substantially the entire collection path between the focussing means and the feedhorn 42. The corrugated feedhorn collects this radiation and converts it into a waveguide mode. The received radiation is fed to the detector 22 and used to image the scanned area of the patient's body.

As mentioned above, the sensitivity profile of the radiation collected in the scanner of FIG. 2 is well-defined. More specifically, the sensitivity profile of the radiation collected is a Guassian profile. It should be noted that the feedhorn 42 and/or lens 40 of FIG. 2 can be considered to act as an antenna. As a result of the reciprocal nature of antennas, the sensitivity profile corresponds to the antenna beam pattern. This means that were the detector to be replaced with a signal source or emitter, the apparatus would emit along the collection path a beam having a fundamental mode Gaussian intensity profile.

In the apparatus of FIGS. 1 and 2, scanning of a target area of a patient's body is effected by rotating the mirror 14. This provides a single line scan. To collect data over a wider area, the housing 8 is mounted on a support (not shown) that facilitates controlled indexing movement of the housing 8 along a direction perpendicular to the scanning direction, indicated by line III of FIG. 1. Indexing occurs at the most once for every revolution of the mirror 14. In order to reduce the effects of noise, the system can be arranged to average the results of a number of successive scans along each respective line. In this case, the mirror undergoes a number of revolutions, for example five, at any given axial position before indexing occurs. This improves the signal to noise ratio of the device. However, it will be appreciated that this is done at the expense of the speed of image acquisition.

Figure 4:
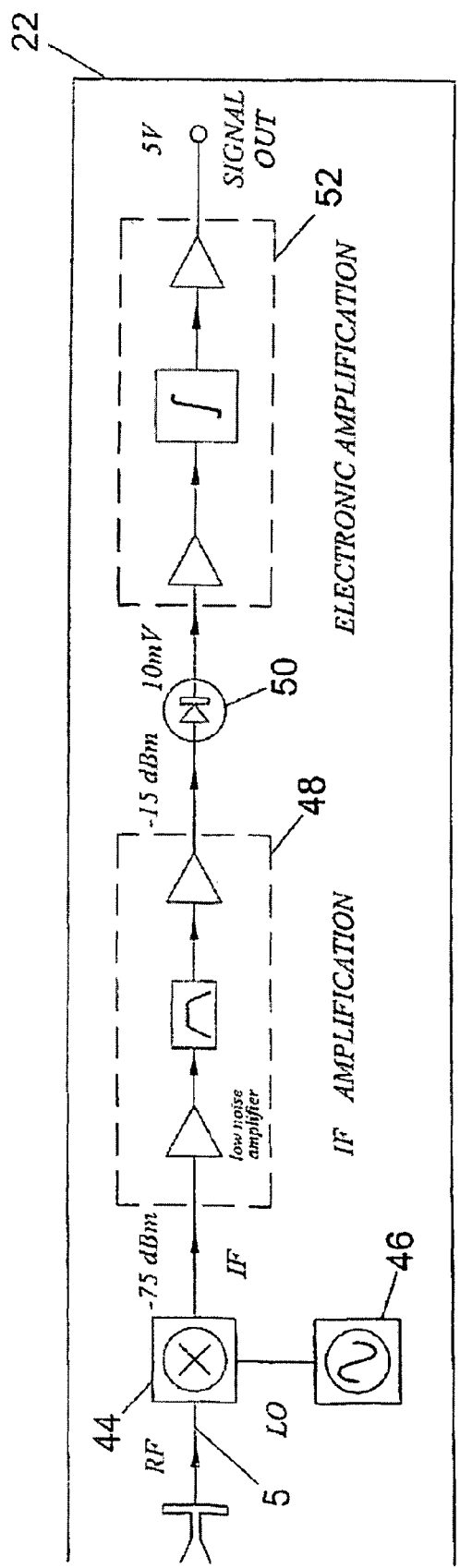
FIG. 4 is a block diagram of a detector circuit for use in the imager of FIG. 2.

FIG. 4 shows an example of a detector or radiometer 22 that can be used in the imager of FIG. 2. This comprises a mixer 44 for combining a received signal 5 with a signal from a local oscillator 46. Connected to the mixer 44 is an IF amplification stage 48 for amplifying and band pass filtering the intermediate frequency IF signal received from the mixer. The output of the IF amplification stage 48 is connected to a square law detector, for example a diode 50. Connected to the output of the diode 50 is an electronic amplification stage 52 that is operable to amplify an incoming signal, integrate it using a low pass filter and amplify the output to give a voltage proportional to the detected power, that is in turn proportional to the brightness temperature of the area being imaged.

The measurement of brightness temperature typically has a temperature sensitivity given by: $\Delta T = T_{sys}(Bt)^{-1/2}$, where $T_{sys}$ is the system noise temperature, B is the pre-detection bandwidth and t is the integration time of the measurement. For a radiometer of given noise, temperature and bandwidth, the temperature sensitivity can be improved by increasing the integration time. This is a trade-off against the image acquisition time. Typical integration times per pixel might be 1-10 ms. This also governs the beam-scanning rate.

The choice of what frequency band to use for the imager depends on a number of factors and is governed by the dielectric properties of body tissue and how they vary with frequency. The frequency band is set by the detector electronics 22 and in particular the oscillator/mixer/filter combination shown in FIG. 4. The most comprehensive publications on the dielectric properties of various tissue types are "The dielectric Properties of Biological Tissues: I. Literature Survey" by Gabriel et al, Phys. Med. Biol., 41, 1996, pp 2231-2249; "The dielectric Properties of Biological Tissues: II. Measurements in the Frequency Range 10 GHz to 20 GHz" by Gabriel et al, Phys. Med. Biol., 41, 1996, pp 2251-2269, and "The dielectric Properties of Biological Tissues: III. Parametric Models for the Dielectric Spectrum of Tissues" by Gabriel et al, Phys. Med. Biol., 41, 1996, pp 2271-2293. These cover measurements of up to 20 GHz. Very little reliable data exists above 20 GHz. Nevertheless, in general a longer wavelength penetrates through more tissue, whereas a shorter wavelength is desirable for good spatial resolution. Shorter wavelengths are reflected less by the skin reducing complications due to reflection of thermal energy from the surroundings. By considering the properties of different tissues, the frequency range for radiometric imaging of the body temperature is 10-200 GHz. Within that range, the 90-100 GHz band gives a reasonable compromise between penetration depth and spatial resolution. Target values for penetration depth and spatial resolution are of the order of a few millimeters.

Figure 5:
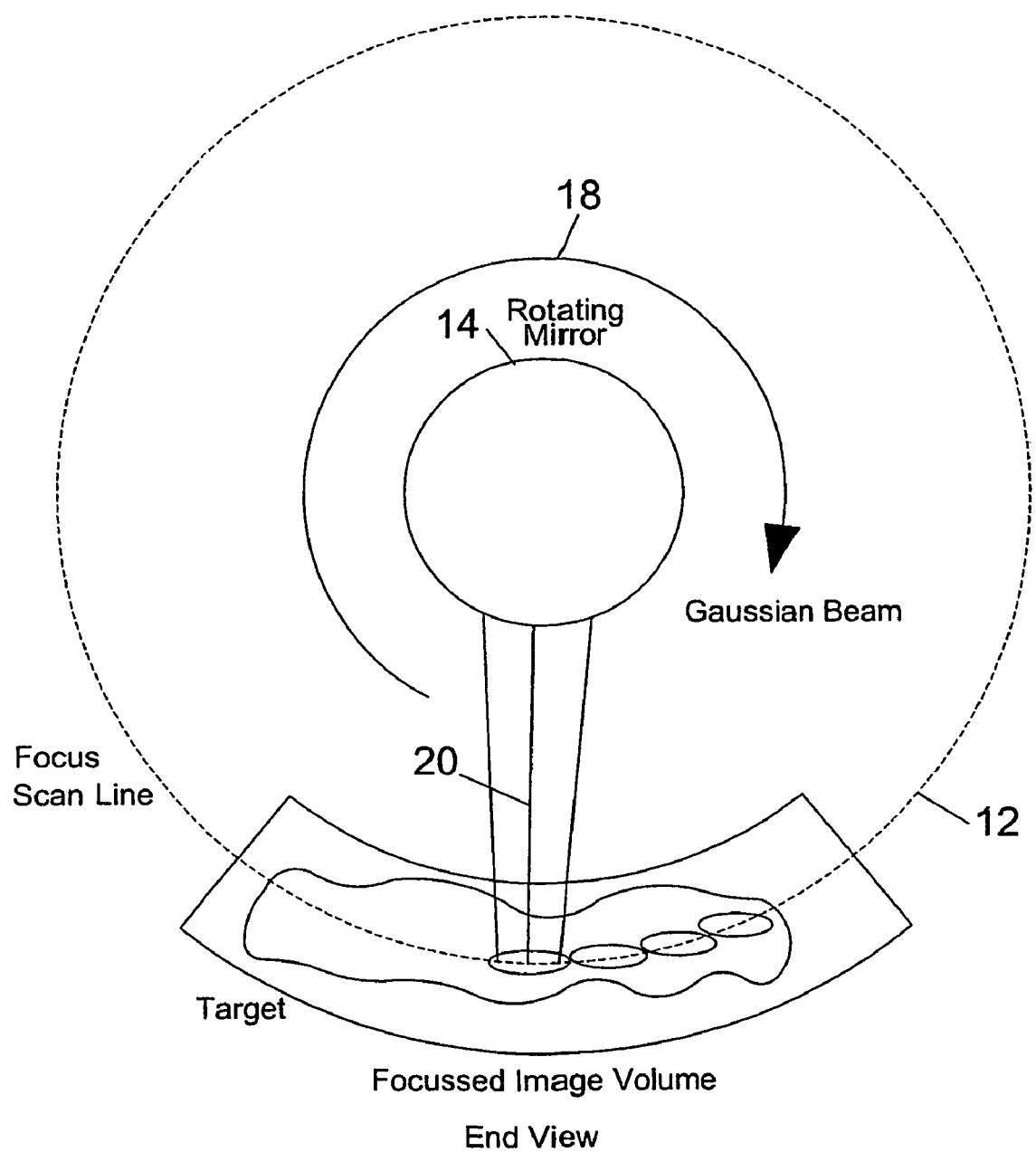
FIG. 5 is an end view of the imager of FIG. 2 that illustrates scanning of a portion of a patient's body.

In use of the apparatus of FIGS. 1 and 2, the mirror 14 is rotated about the axis 16 so that an area of the patient's body can be scanned. As shown in FIG. 5, when the mirror 14 rotates, the collection path is swept through 360°, and so the scan line 12 is in the form of a circumference swept out by the path. In FIG. 2, the lines 24 and 26 indicate a collection path along which millimeter wave electromagnetic radiation travels from a spot 60 to be imaged by the apparatus to the mirror 14. Received radiation is reflected from the mirror 14 and passed through the isolator 28 and then travels through the focussing lens 40 and into the corrugated feedhorn 42.

Figure 6:
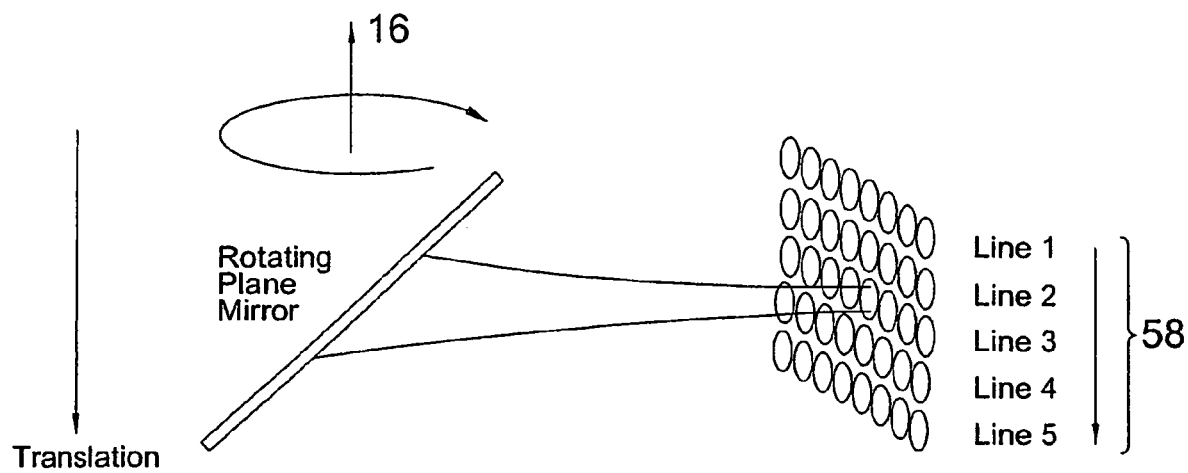
FIG. 6 shows a first technique for scanning an area of a patient's body.
Figure 7:
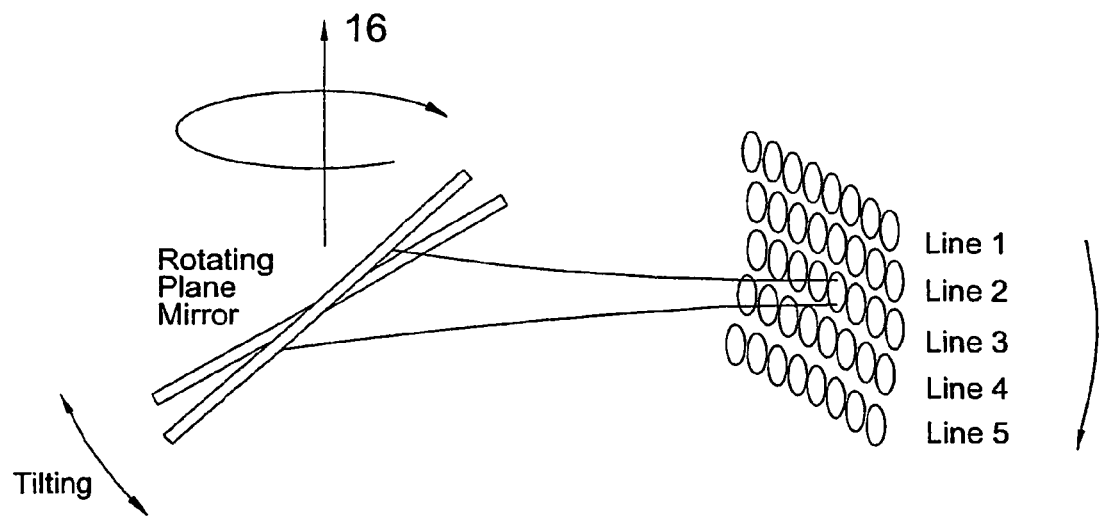
FIG. 7 shows a second technique for scanning an area of a patient's body.

The imager 1 acquires the image of a part of the body by obtaining image data from each successive one of a number of areas in a single scanning line and then repeating the process for successive lines thereby building up an array of imaged areas. Where the mirror is rotatable about a single axis, as shown in FIGS. 2 and 6, the array of areas lies on a surface of a notional cylinder, and this correspondingly governs the plane of the captured image. In this case, the mirror makes a single sweep, or a plurality of such sweeps, at a given level, say line 3 of FIG. 6. Then the scanner is moved translationally, so that the next line can be scanned. In this way, an array 58 of scanned areas is built up. Alternatively, where the mirror 14 is rotatable about two perpendicular axes, scanning could be performed in two dimensions, as shown in FIG. 7. This approach causes the apparatus to scan a volume that is part of the surface of a sphere, i.e. curved in two planes. In this case, translational movement of the housing of the imager is not necessary.

Figure 8:
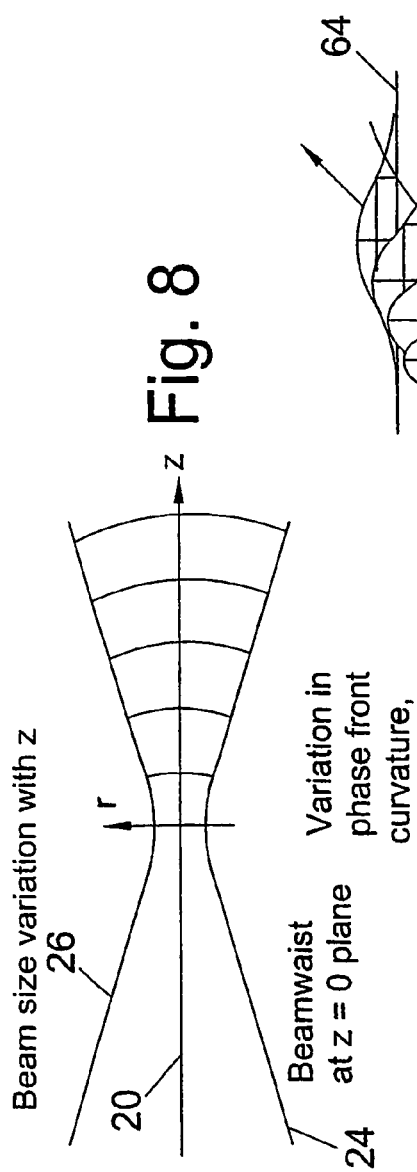
FIGS. 8-10 illustrate the sensitivity distribution profile and beam pattern associated with the apparatus shown in FIG. 2.
Figure 10:
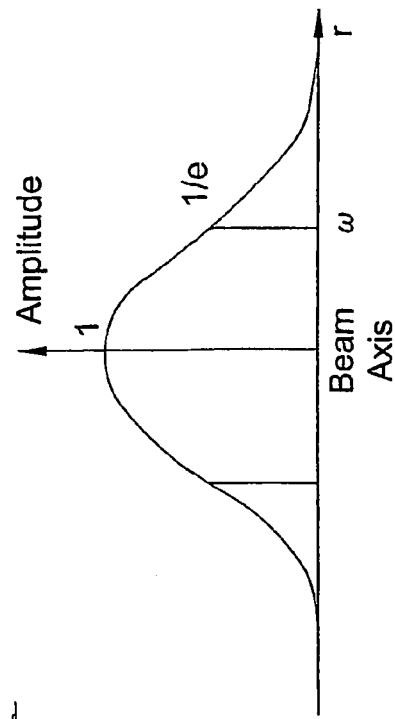
Figure 9:
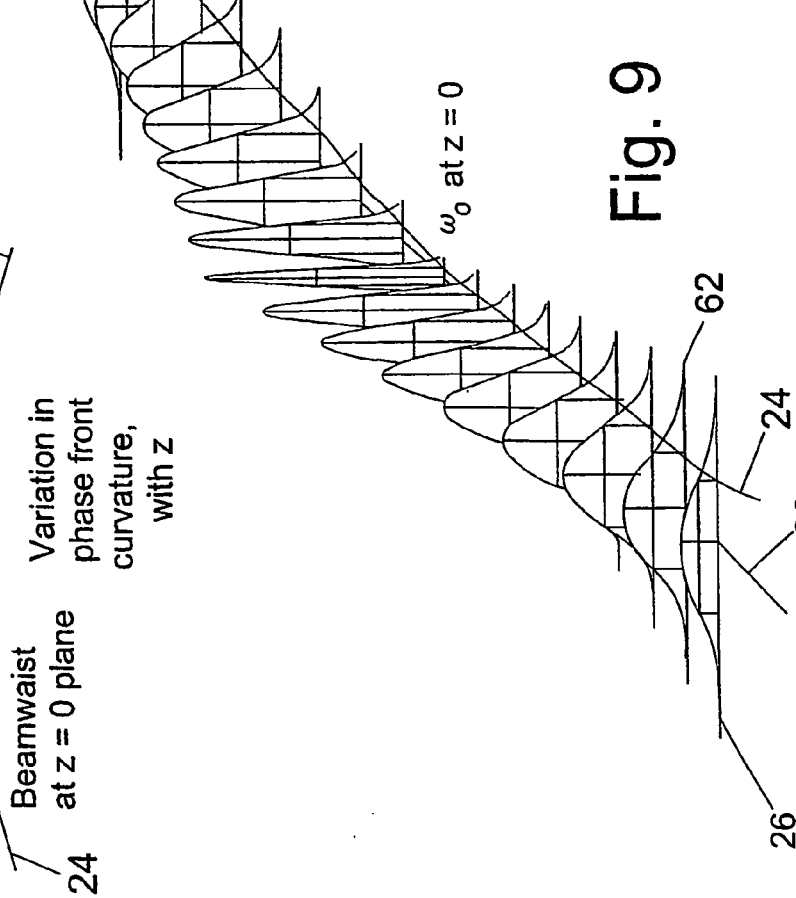

For any given position of the mirror 14, the apparatus is focused on a respective spot 60 on the cylindrical surface. The sensitivity of the apparatus to incident radiation across that spot varies, as shown in FIGS. 8 to 10. This sensitivity profile has a fundamental mode Gaussian form. FIG. 8 shows the sensitivity profile at various different points along the beam from a position some way in front of the point z=0, see profile 62, to a position somewhere behind, see profile 64. As can be seen, the profile retains its fundamental mode Gaussian form, but the width of the peak progressively decreases from the profile 62 to a minimum width at the plane z=0, whilst the peaks behind the plane z=0 become progressively broader with increasing distance from the plane. The Gaussian mode is preserved throughout the optical path, and enables the width of the collection path to be comparable with the wavelength of operation, the profile enabling the effects of diffraction to be anticipated or controlled. The mode of the imager is preserved principally because of the configuration of the feedhorn 42.

Figure 11:
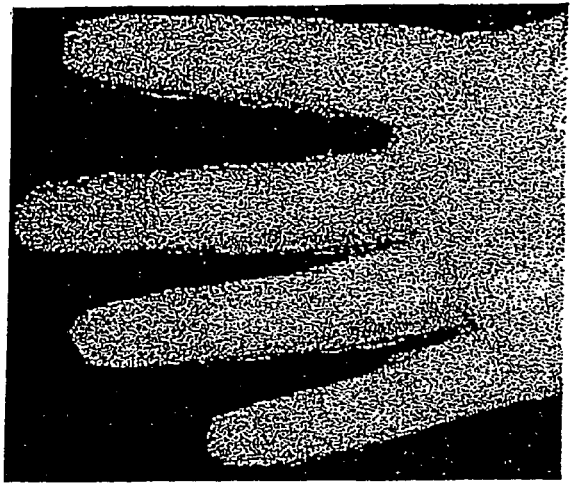
FIG. 11 shows visible, infrared and millimeter wave images of a part of a human hand.
Figure 11:
Figure 11:
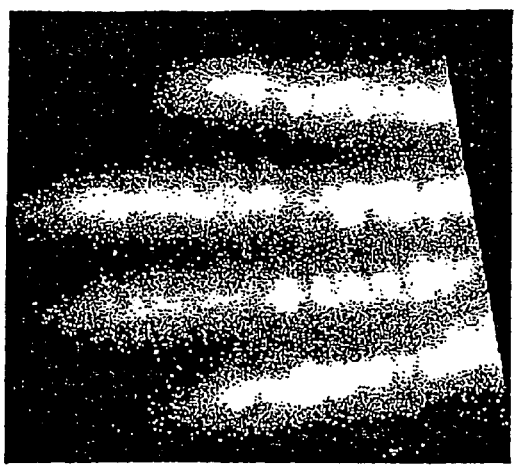

The radiometer in which the invention is embodied allows features below the surface of a patient's body to be imaged. To illustrate this and compare the effectiveness of the radiometer in which the invention is embodied with existing techniques, FIG. 11 shows three scanned images. The first was taken using visible radiation. As would be expected, visible light is unable to distinguish features below the surface of the patient's hand. The second image was taken using infrared radiation. In this case, a small amount of sub-surface detail can be seen at the patient's finger tips. The third image was taken using the radiometer of FIGS. 1 and 2. In this case, thermal variations are clearly distinguishable. Providing images of this nature is advantageous.

Figure 12:
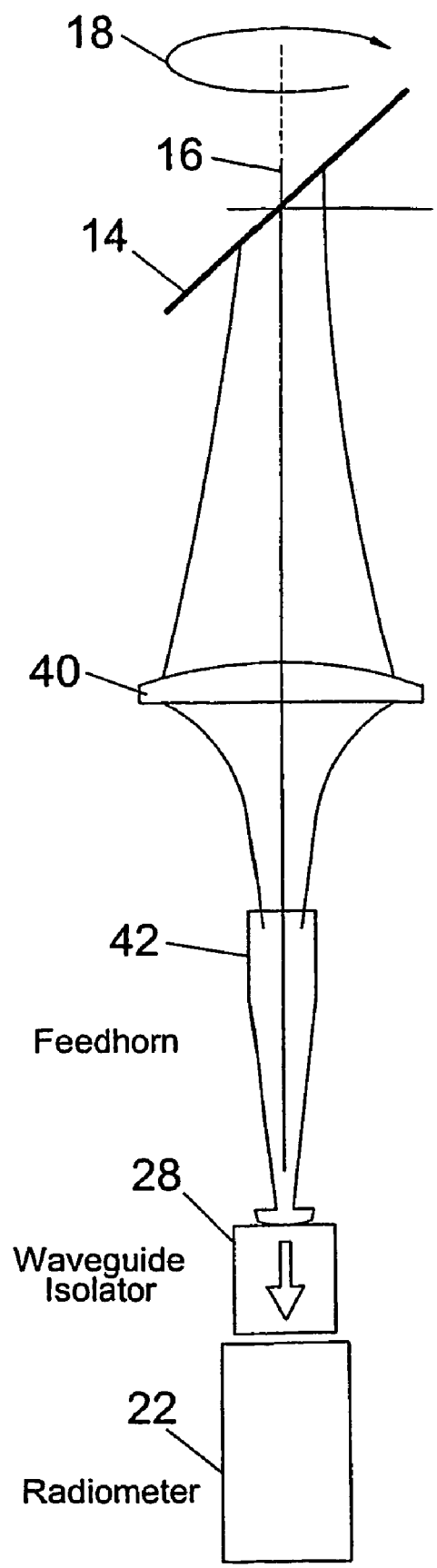
FIG. 12 is a schematic diagram of a modified version of the imager of FIG. 2.
Figure 13:
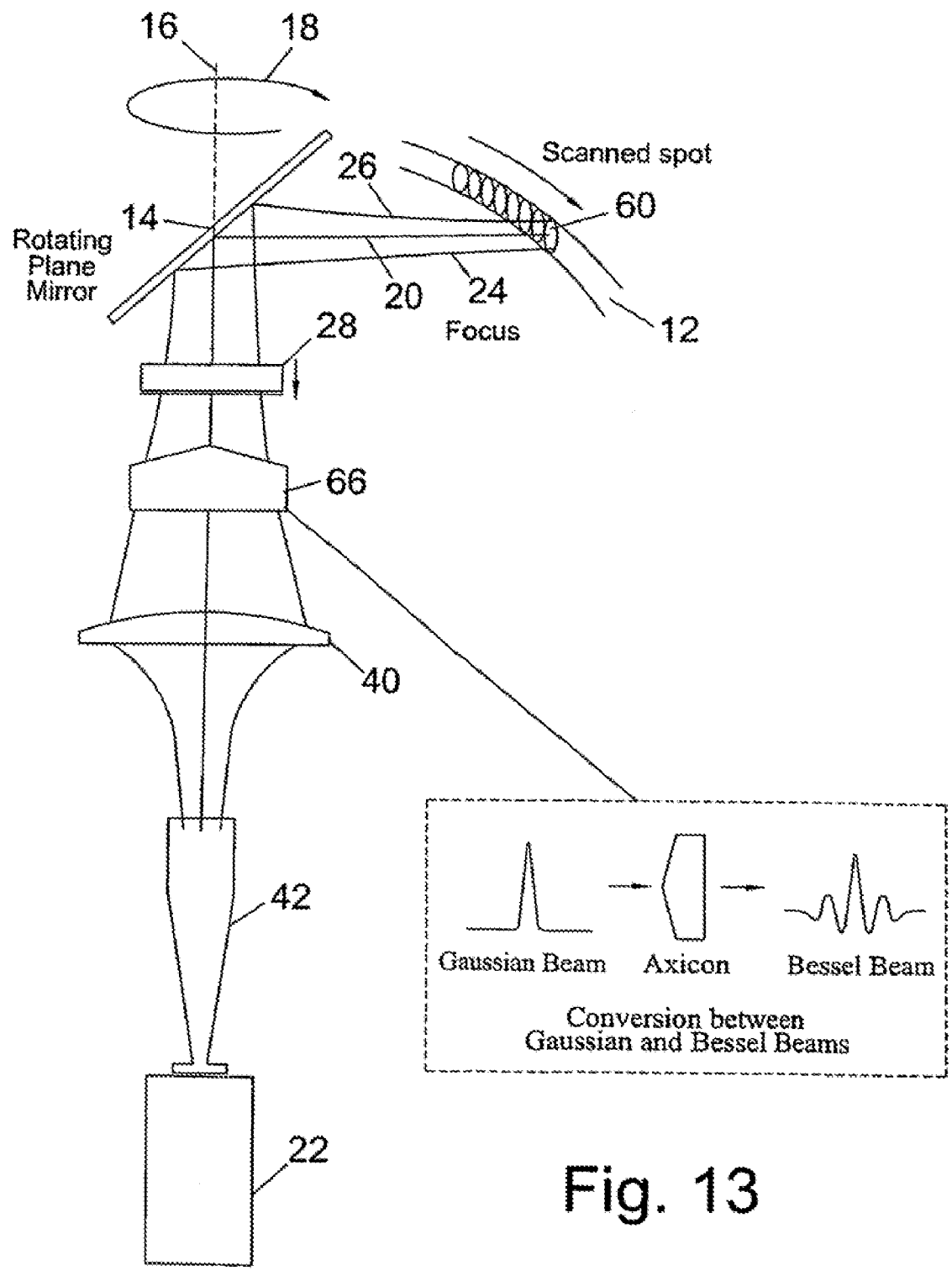
FIG. 13 is a schematic diagram of another modified version of the imager of FIG. 2.

Various modifications to the imager of FIG. 2 are possible. For example, rather than having the isolator 28 of FIG. 2 between the mirror 14 and the lens 40, it could be located between the feedhorn 42 and the radiometer 22, as shown in FIG. 12. Additionally or alternatively, the apparatus can be modified by the inclusion of an axicon 66, as shown FIG. 13. This is located in the collection path between the mirror 14 and the lens 40 and is operable to convert between a Gaussian sensitivity profile and a Bessel sensitivity profile 68, as can be seen from the inset to FIG. 13. The Bessel profile has a central peak that diffracts less over a given distance compared with a fundamental Gaussian profile of the same width. This may improve the depth of field of the apparatus.

Figure 14:
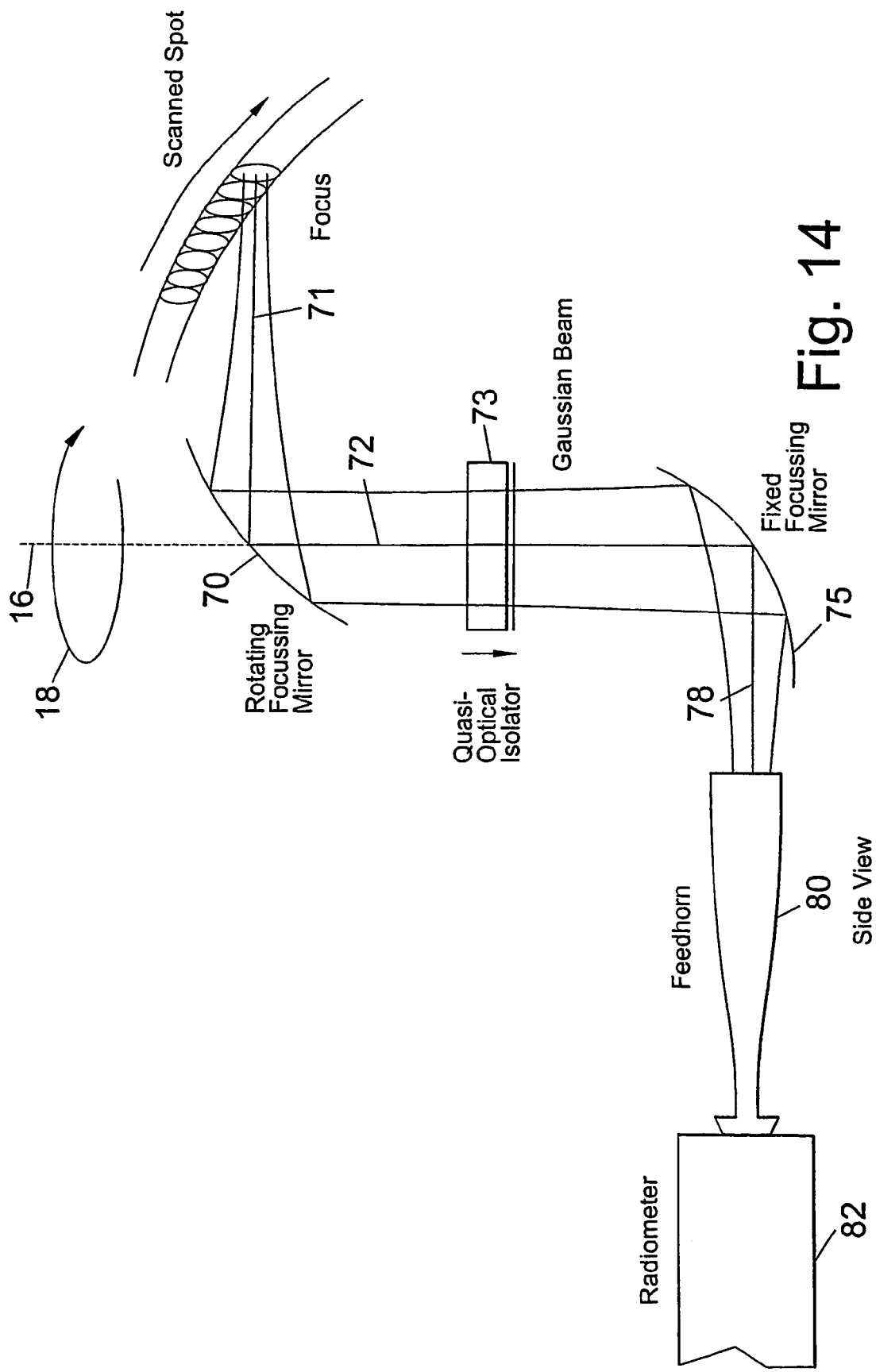
FIG. 14 is a schematic diagram of another imager for use in the arrangement of FIG. 1.

FIG. 14 shows another apparatus in which the invention is embodied. In this, scanning is effected using a curved, rotatable mirror 70. This is positioned so as to direct radiation incident on it from a first optical path 71 into another, orthogonal path 72. Located on this path 72 are in sequence a quasi-optical isolator 73 and another, second curved focussing mirror 75. This second mirror 75 is fixed and is positioned to fold radiation incident thereon into another orthogonal path 78. Located on this second path 78, is a feedhorn 80, preferably a corrugated feedhorn, which is connected to a detector 82. Radiation collected in the feedhorn 80 is fed to the detector 82, where it can be processed to provide a suitable image of the scanned area. An advantage of using curved mirrors 70 and 75 is that they can be formed of materials that dissipate less of the received radiation than a lens.

Figure 15:
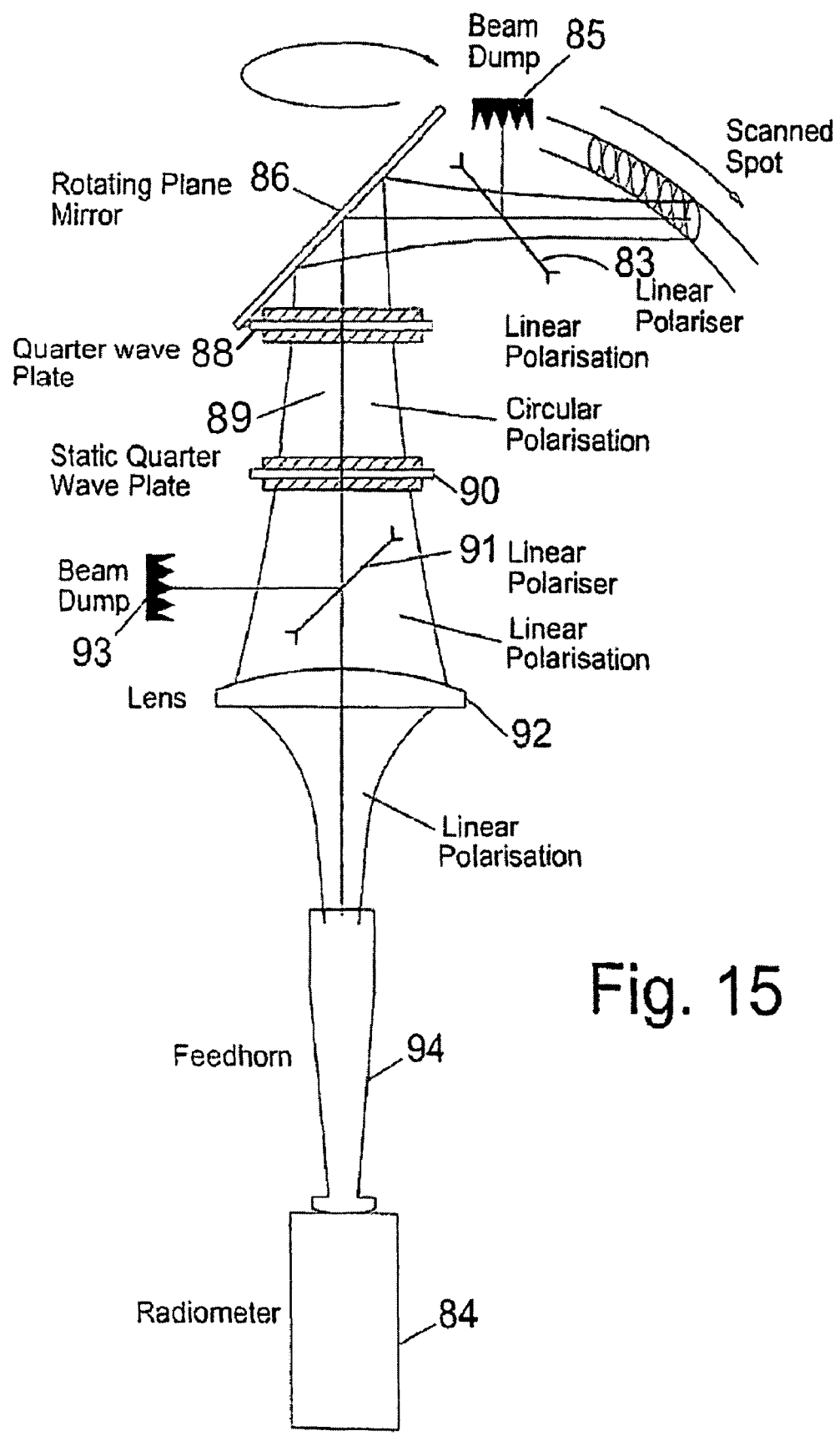
FIG. 15 is a schematic diagram of yet another imager for use in the arrangement of FIG. 1.

FIG. 15 shows a yet further example of an imager in which the invention is embodied. In this case, the radiometer 84 is linearly polarised. The polarisation of the signals received from the lines scanned by the mirror can vary with the angle from which they are received. This may or may not be a problem depending upon what target is being sensed. For targets that are largely unpolarised, such as body tissue, it may not matter. If, however, it is considered important to have a fixed polarisation at the target, this can be achieved with the addition of two quarter-wave plates.

FIG. 15 shows an imager that is adapted to provide a fixed polarisation. This imager includes a linear polariser 83 that is positioned in the collection path so as to direct unwanted cross-polarised radiation into a first beam dump 85 and direct polarised radiation to a rotating mirror 86. The input linear polariser 83 can optionally be attached to the mirror 86. Alternatively, the input linear polariser 83 could be fixed, in which case it would take the form of a cylinder or any other suitable shape that would be in the line of view of the target. The mirror 86 directs radiation received from the polariser 83 along a collection path to a first quarter wave plate 88, which is attached to the rotating mirror 86. When the input is linearly polarised, this radiation is converted by the rotating quarter wave plate 88 to circularly polarised radiation.

On the collection path 89 after the first quarter wave plate 88 is a second quarter wave plate 90, which converts the circularly polarised output from the first plate into linearly polarised radiation. The second quarter wave plate 90 is aligned with the polarisation of the radiometer, so that radiation downstream from the second plate 90 is polarised at an angle that is suitable for reception by the linearly polarised radiometer 84. Next on the collection path 89 is a linear polariser, more specifically a vertical polariser 91 that is positioned so as to direct unwanted cross-polarised radiation into a beam dump 93. After the vertical polariser 91 are a lens 92, and a linearly polarised feedhorn 94 for feeding radiation to the linearly polarised detector 84. Since the feedhorn 94 is in front of the detector, it is the feedhorn 94 that defines the orientation of the polarisation. By providing the first and second quarter wave plates, the radiation received by the detector is correctly polarised.

Figure 16:
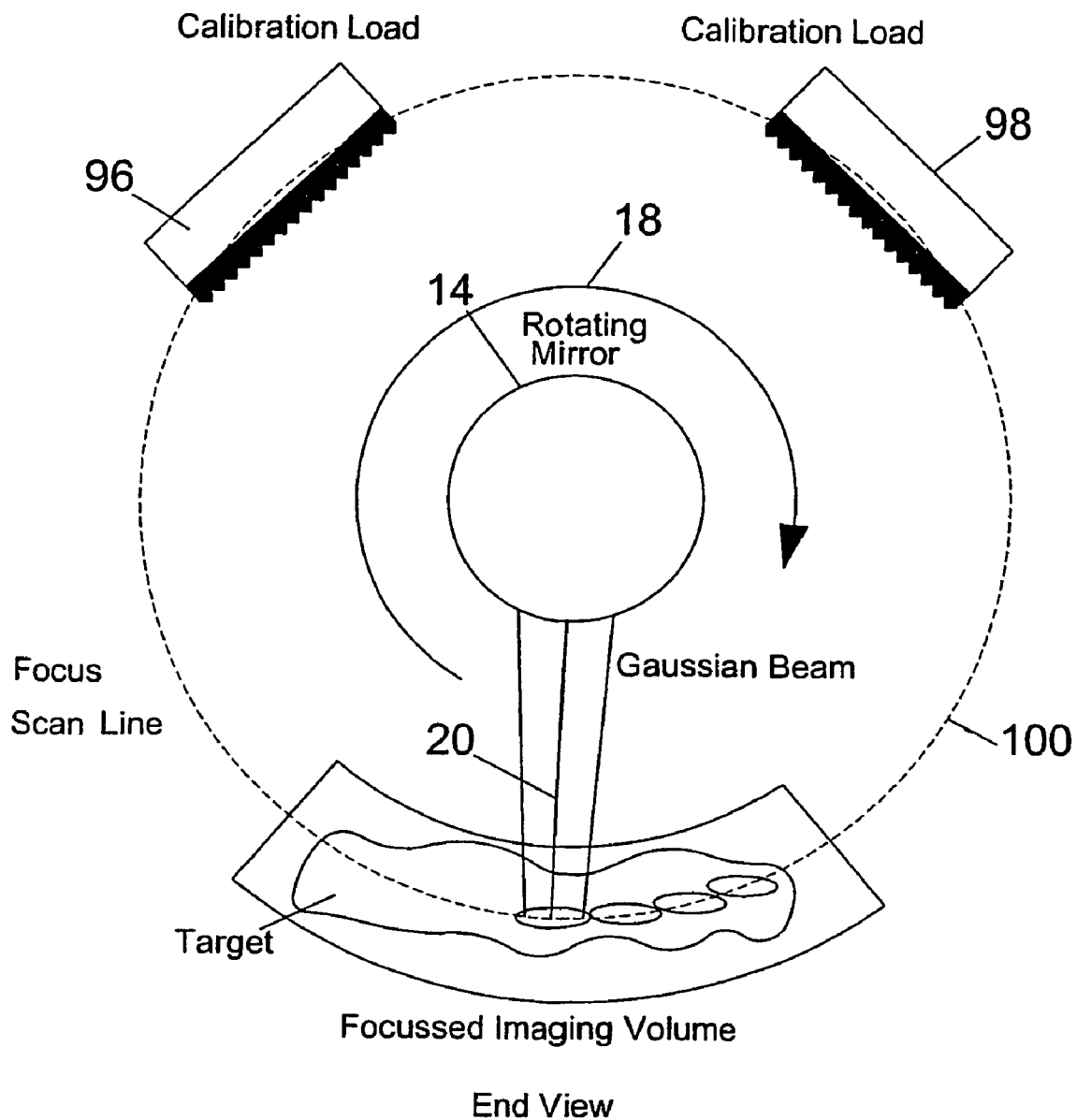
FIG. 16 is an end view of an imager in which calibration loads are included on the radiation collection path.

In all of the imagers described above, it is important that calibration be carried out. To this end, two angularly spaced calibrations loads 96 and 98 may be provided in a part of the scan or the collection path that does not include the target, as shown in FIG. 16. Hence, when the scanning mirror is rotated, the scan line 100 intercepts not only the area of the patient that is to be scanned, but also the calibration loads 96 and 98. This means that the calibration loads 96 and 98 are sensed every rotation of the scanning mirror. This leads to a high rate of repetitive calibration, which can be used to reduce the effects of gain variations in the radiometer that cause sensitivity fluctuations. Also, this line-by-line calibration reduces artefacts in the image, such as stripes, caused by sensitivity fluctuations.

To perform calibration of the radiometer, it is preferable to use two thermal targets having temperatures above and below the range of temperatures expected in the real scene. To this end, one of the calibration loads 96 is a hot load and the other 98 is a cold load. Any suitable calibration loads could be used. For accurate radiometric calibration, it is desirable to have the thermal target filling the beam of the radiometer and a uniform, known temperature over that area. The temperature should be constant during the time taken to make the calibration. Preferred examples of the calibration loads are shown in FIGS. 17 to 19.

Figure 17:
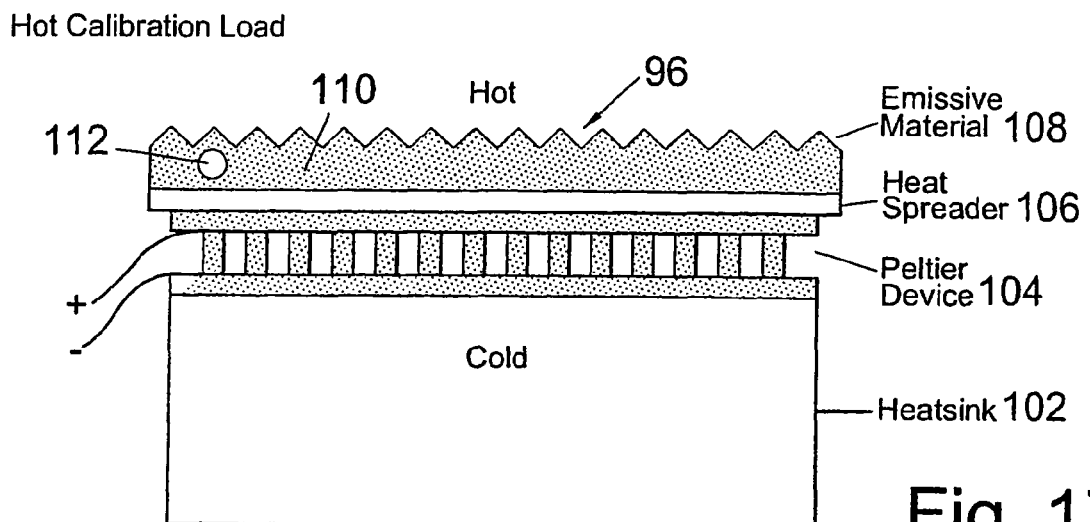
FIG. 17 is a cross section of a hot calibration load for use in the arrangement of FIG. 16.
Figure 18:
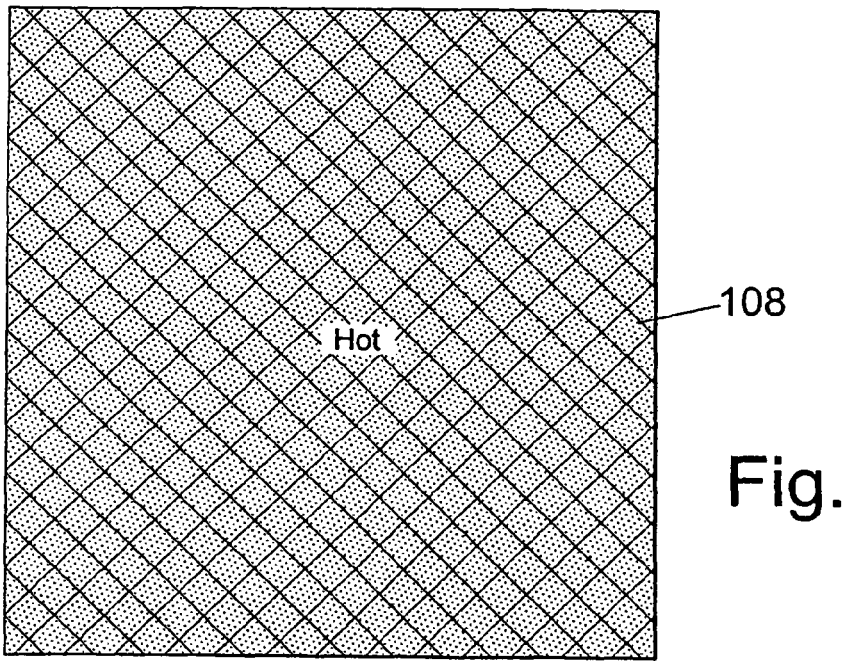
FIG. 18 is a plan view of the load of FIG. 17.
Figure 19:
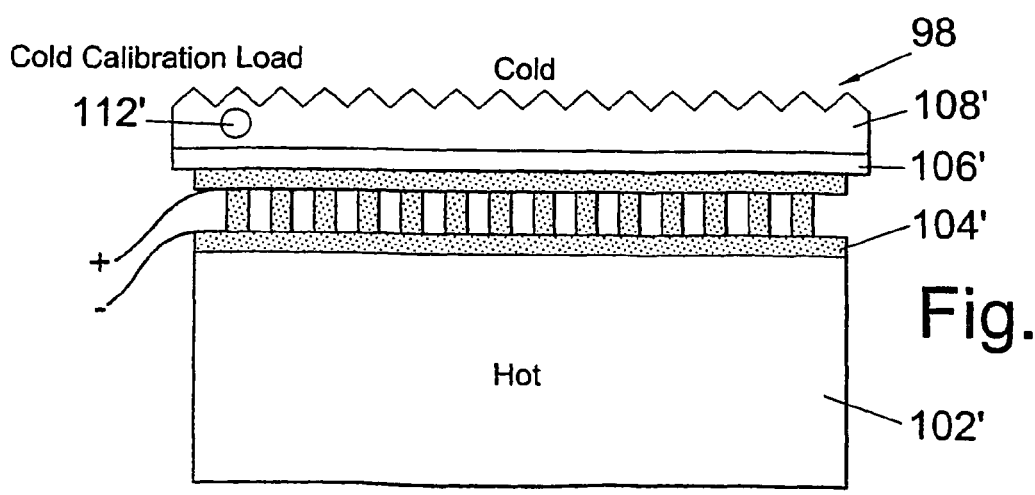
FIG. 19 is a cross section of a cold calibration load for use in the arrangement of FIG. 16.

FIGS. 17 and 18 show a hot calibration load 96. This comprises a heat sink layer 102 carried on which is a thermoelectric heating element 104, for example a Peltier element. By applying an appropriate current to the Peltier element, the load 96 can be heated. On the element 104 is a heat spreader layer 106. This is a thin thermally conducting plate, e.g. metal that evens out any small scale temperature variations on the face of the Peltier device 104 and provides a relatively uniform temperature distribution. On the heat spreader layer 106 is an emissive plate 108, which has sufficient thermal conductance to ensure that its temperature can be controlled when in contact with a hot or cold plate. To achieve a uniform temperature across the emissive plate 108 with a minimum of thermal gradient towards the edges and corners, the heat spreader 106 preferably has the same surface area as the emissive plate 108, and is as big as or slightly larger than the Peltier device 104.

The material of the emissive plate 108 is chosen to have an emissivity $\in$ close to unity in the frequency range of operation ensuring that its brightness temperature $T_B$ is very close to its physical temperature $T_P$, since $T_B = \in T_P$. Having a high emissivity means the material is also a good absorber in the frequency range of interest. A suitable emissive material could be a solid microwave absorber, rather than a porous structure as is the case for many electromagnetic absorbers, such as Eccosorb MF-110 provided by Emerson & Cuming. The plate 108 should be thin enough to avoid the setting-up of too great a thermal gradient from the back to the front surface when the thermoelectric element is operated. It is also preferable that the plate has a front surface, which is rough with respect to the wavelength of operation, because this minimises any specular reflections from the surface. In the present example, this is achieved by having an outer surface in which regular pyramids 110 are formed.

As noted before, it is desirable to have a substantially uniform and constant temperature over the surface of the emissive material. To monitor the temperature of the emissive plate a thermometer or thermocouple 112 is provided. This is embedded in the bulk of the material of the plate 108 so that any variations in temperature are known. Optionally, multiple thermometers may be used to monitor spatial variations in temperature. In any case, connected to the thermometer or thermocouple 112 is temperature measurement circuitry for monitoring the temperature (not shown). Control circuitry can also be connected to the Peltier element 104, so that in the event that changes in temperature are detected, a control signal can be sent to alter the current applied to the Peltier element 104, thereby to cause the temperature to return to a pre-determined value.

FIG. 19 shows the cold calibration load 98. This is identical to the hot load except the Peltier device is arranged to operate as a thermoelectric cooling device for the emissive plate. This can be done by selecting an appropriate current.

A large difference in temperature between the hot and cold loads 96 and 98 is desirable provided that the response of the radiometer behaves predictably over that range. However, the temperature difference is typically limited by practical considerations. For example when operating in normal atmospheric conditions, too cold a temperature would cause condensation and ice to form on the surface of the emissive material, which could alter its apparent brightness temperature. Hence, for a radiometer measuring body temperatures calibration load temperatures could be in the range of 5 to 10° C. for the cold load and 50 to 60° C. for the hot load.

The emissive plates of the hot and cold loads 96 and 98 respectively provide the thermal targets that are used to calibrate the response of the radiometer. When these loads are incorporated into the imagers shown in FIGS. 2 and 12 to 15, their location and temperatures are stored by control software provided in the computer 4. This information is used to calibrate real measurements of a target area of a patient's body. In use of the imagers, radiation emitted from the loads is detected for each line of the scan. This means that calibration can be done on a line-by-line basis, thereby making the imager both sensitive to overall system changes and accurate. Techniques for calibrating imagers are known and so will not be described herein in detail.

A skilled person will appreciate that variations of the disclosed arrangements are possible without departing from the invention. For example, whilst the imagers described previously in detail each include a rotatable mirror so that the collection path rotates, these could equally be adapted to provide a raster scan of a target area of a patient. Accordingly, the above description of a specific embodiment is made by way of example only and not for the purposes of limitation. It will be clear to the skilled person that minor modifications may be made without significant changes to the operation described.

The invention claimed is:

1. A non-contact passive medical scanning imager for imaging subcutaneous body temperature comprising:
   a scanner configured to scan a target area of a patient;
   a detector configured to sense millimeter wave electromagnetic radiation that is emitted from the target area of the patient;
   a collector configured to collect the radiation that is emitted from the target area of the patient and directing that radiation along a collection path to the detector in such a manner that the collected radiation has a defined sensitivity profile across and along substantially the entire length of the collection path;
   electronic circuitry configured to generate image data associated with the target area of the patient based on the collected radiation; and
   an isolator in the collection path of the collected radiation configured for preventing signal leakage from the detector towards the patient's body.

2. An imager as claimed in claim 1, wherein the collector comprises a corrugated feedhorn.

3. An imager as claimed in claim 1, wherein the collector comprises a waveguide configured to supply radiation to the detector.

4. An imager as claimed in claim 1, wherein the collected radiation has a Gaussian sensitivity profile.

5. An imager as claimed in claim 2, wherein the feedhorn is configured to convert a fundamental Gaussian mode beam of radiation into a waveguide mode in which radiation propagates through a wave guide to the detector.

6. An imager as claimed in claim 1 wherein the collected radiation has a Bessel sensitivity profile.

7. An imager as claimed in claim 6 including an axicon in the path of the collected radiation and configured to convert a Gaussian sensitivity profile of the collected radiation to the Bessel sensitivity profile.

8. An imager as claimed in claim 1 wherein the collector includes means for focusing.

9. An imager as claimed in claim 1, wherein the scanner is configured to rotate 360° about an axis in the collection path.

10. An imager as claimed in claim 9, wherein the scanner comprises a deflector that is rotatable about one axis to scan the collection path in a scanning direction across a body.

11. An imager as claimed in claim 10 further comprising a support that facilitates controlled line-indexing for moving the collection path in a direction perpendicular to the scanning direction.

12. An imager as claimed in claim 11, wherein the support is operable to swing the deflector about a second axis perpendicular to the one axis.

13. An imager as claimed in claim 1, wherein the imager is operable to form an image from emitted radiation in the frequency range of 90-100 GHz.

14. An imager as claimed in claim 1, further comprising at least one calibration load for emitting millimeter wave radiation at a pre-determined intensity, the collector being operable to direct said radiation to the detector to enable the imager to be calibrated.

15. An imager as claimed in claim 14, wherein the calibration load is provided in the collection path of the imager, so that the imager can be calibrated for each pass of the collector.

16. An imager as claimed in claim 14, wherein the at least one calibration load comprises two calibration loads, further comprising means for maintaining the two calibration loads at different temperatures, the temperatures straddling a range of subcutaneous body temperatures to be imaged.

17. An imager as claimed in claim 1 wherein the detector is linearly polarized.

18. An imager as claimed in claim 17 further including polarization means for altering the polarization of received radiation to be aligned with the polarization of the detector.

19. An imager as claimed in claim 1 wherein the scanner scans the target area of the patient such that the collection path is in the form of a circumference of a notional cylinder at each of a plurality of indexed steps.

20. An imager as claimed in claim 1 wherein a spot on the collection path resides on a focal plane of the scanner, such that the sensitivity profile is symmetrical and reduced about the spot along the collection path.

21. An imager as claimed in claim 1 wherein the defined sensitivity profile is non-uniform across and along the collection path based on known changes in a location of a focal spot of the scanner along the collection path.

22. An imager as claimed in claim 1, wherein the isolator comprises a quasi-optical isolator.

23. An imager as claimed in claim 1, further comprising a computer configured to display an image associated with data of the collected radiation corresponding to the subcutaneous body temperature of the patient.

* * * * *